US00PP08791P

United States Patent [19]

Jack et al.

[11] Patent Number: Plant 8,791

[45] Date of Patent: Jun. 21, 1994

[54] CHAMELAUCIUM (WAXFLOWER) PLANT NAMED REVELATION

[75] Inventors: Brian Jack; Victoria Syme, both of Coorow, Australia

[73] Assignee: New World Plants, Escondido, Calif.

[21] Appl. No.: 113,051

[22] Filed: Aug. 23, 1993

[51] Int. Cl.[5] ..... A01H 5/00

[52] U.S. Cl. ..... Plt./54.1

[58] Field of Search ..... Plt. 54.1

*Primary Examiner*—James R. Feyrer

*Attorney, Agent, or Firm*—Christie, Parker & Hale

[57] ABSTRACT

A new and distinct interspecific Chamelaucium hybrid variety of shrub (known popularly as waxflower or Geraldton waxflower) particularly distinguished by its unique ability to change its initial flower petal color from white at anthesis to violet/mauve in the course of five to seven days, its ability to hold open its flowers for an extended period of time, its excellent post-harvest performance as a fresh cut flower and its unique and very striking floral display with flowers of different colors present at the same time. The new plant is further distinguished by its profuse spring blooming habit, vigor and strong erect growth.

3 Drawing Sheets

BACKGROUND OF THE NEW PLANT

The new plant is an interspecific Chamelaucium hybrid shrub variety originated from a deliberate and controlled cross between two different species selections. An unnamed, unpatented variety of Chamelaucium megalopetalum was used as the seed parent and the Chamelaucium uncinatum variety 'Purple Pride' (unpatented) was used as the pollen parent. This controlled cross-pollination was performed at Western Flora, Coorow, Western Australia, Australia. Once the actual act of cross-pollination was executed, a period of 20 days elapsed until the immature seed pod was harvested so aseptic dissection could occur resulting in the removal of the developing ovules/embryos. Once these ovules/embryos were removed, they were transferred onto a nutrient agar-based media so that they could continue to develop, eventually resulting in mature flowering plants. After the plants matured and flowered for several seasons one plant stood out above the rest of its siblings due to its uniquely different floral display and vigorous upright growth.

The new variety has been asexually propagated, by cuttings at the above identified location, for succeeding generations and has been found to be stable and to continue to maintain its unique floral display, possessing flowers of different color at the same time.

BRIEF DESCRIPTION OF ILLUSTRATIONS

The accompanying color photographs show typical specimens of the flowers of the new variety depicted in color as nearly true as it is possible to make in color illustrations of this character. The photographs show the new variety's unique characteristic whereby flower petals change color over a period of time, up to 14–15 days, from white or near white at anthesis to violet/-mauve.

Three different stages are illustrated, from near white (1) through an interim stage of light mauve (2), to the deepest flower coloration of violet/mauve (3).

DETAILED DESCRIPTION of 'Revelation'

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions, as well as phenotypic expression, may deviate from the stated values and description depending upon varying environmental, seasonal, light and cultural conditions.

The information provided herein is based on observations of plants grown at Escondido, Calif. The height of plant and flower and foliage size are established as an average using standard commercial cultural practices.

THE PLANT

Origin: Obtained by ovule/embryo rescue done "in vitro".

Parentage:

*Pollen parent.*—Chamelaucium uncinatum 'Purple Pride' (unpatented).

*Seed parent.*—A selected form of Chamelaucium megalopetalum (unpatented).

Classification:

*Horticultural.*—An interspecific Chamelaucium hybrid of a semi-hardy woody shrub.

*Commercial.*—Hybrid waxflower.

Form: Erect branched shrub.

Height: About 1.5–2.0 meters.

Growth: Vigorous, rigid upright, semi-open shrub.

Foliage: Aromatic.

*Quantity.*—Abundant on one- and two-year-old wood; occurring in opposite pairs; spaced about ±14 mm apart on the stem.

*Leaf size.*—About 19 mm long and 1.5 mm wide.

*Leaf texture.*—Flattish, small, marrow, sessile.

*Texture.*—Thick.

*Aspect.*—Glabrous.

*Color.*—Deep green sometimes with a little anthocyanin present.

THE BUD

Form: Rounded; covered with thin deciduous bracteoles.

Size: Approximately globular with a diameter of about 7–8 mm just prior to anthesis.

Color: Bronzy red.

Peduncle:

*Length.*—About 11–13 mm.

*Character.*—Erect.

*Color.*—Green.

THE FLOWER

Blooming habit: Annually and mid-season; flowering once a year in the spring.

Size of flower: Medium with an approximate diameter of about 18 mm.

Borne: On thin first-year stems on the upper axils to form terminal clusters.

Shape: Flattened cup-shaped with rounded slightly cupped, orbicular petals.

Petalage:

*Number.*—Five with five calyx lobes which appear alternately between the petals.

*Arrangement.*—Rotate.

*Form.*—Slightly cupped, orbicular.

*Size.*—About 8 mm in diameter.

*Aspect.*—Waxy.

*Color.*—The new variety has the ability to produce flowers with petals which change color from white or near white at anthesis, to violet/mauve, near RHS 84B, over 5 to 15 days. Initial flower petal coloring is near white; after a few days petals begin to show light magenta, near 65A, largely as washing infused against a near white background until magenta coloration takes over substantially the entire petal, possibly leaving only slight white or near white margins. At this stage flowers with both near white and magenta coloring appear at the same time. As flowers continue to age, petals initially magenta-colored deepen in tonality toward violet/mauve, almost as deep as near 84B to 84A in veination, and with deeper red/purple coloring. At this stage mixtures of flower coloration appear with some flowers having a few near white petals and flower coloring progressing through the aforementioned stages, including flowers with deeply toned petal coloration. Flower centers also change color over time, from light to dark yellow/green to deep red/purple.

Peduncles:

*Length.*—About 11–13 mm; held out and upright.

*Color.*—Green.

Fragrance: Aromatic only when crushed.

Lasting quality: The flower is very long-lasting both on the plant and as a fresh cut flower.

THE REPRODUCTIVE ORGANS

Stamens:

*Number.*—10, with 10 infertile staminodes alternating between each stamen and also attached to the staminal rim.

Anthers:

*Size.*—About 0.7 mm wide at anthesis.

*Color.*—Near RHS 200D at anthesis.

Filaments:

*Length.*—About 2.5 mm.

*Color.*—White.

Pollen:

*Color.*—Greenish brown.

*Texture.*—Waxy and sticky.

Pistils:

*Number.*—One.

Style:

*Length.*—About 7 mm.

*Color.*—White at anthesis, progressing to near RHS 84B about 7 days after anthesis.

Stigma:

*Color.*—Near RHS 17B at anthesis.

*Texture.*—Bearded and hairy.

THE FRUIT

Shape: Hemispherical.

Structure: A three-celled capsule formed by the hardened base of the persistent calyx.

I claim:

1. The new and distinctive variety of Chamelaucium interspecific hybrid plant, substantially as herein shown and described, characterized in particular by flowers with petals changing color from white at anthesis to violet/mauve at maturity and by having flowers of different colors present at the same time.

* * * * *

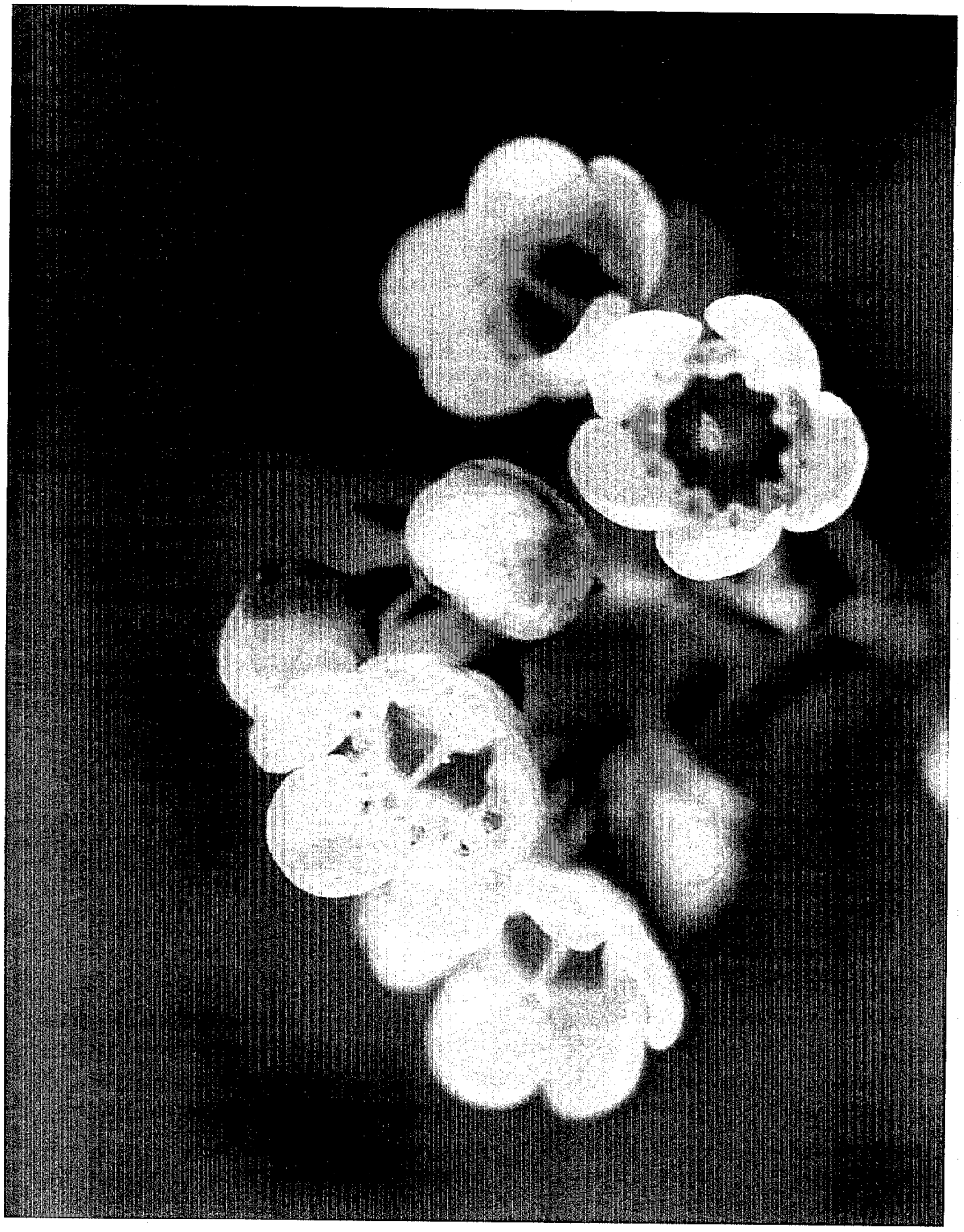

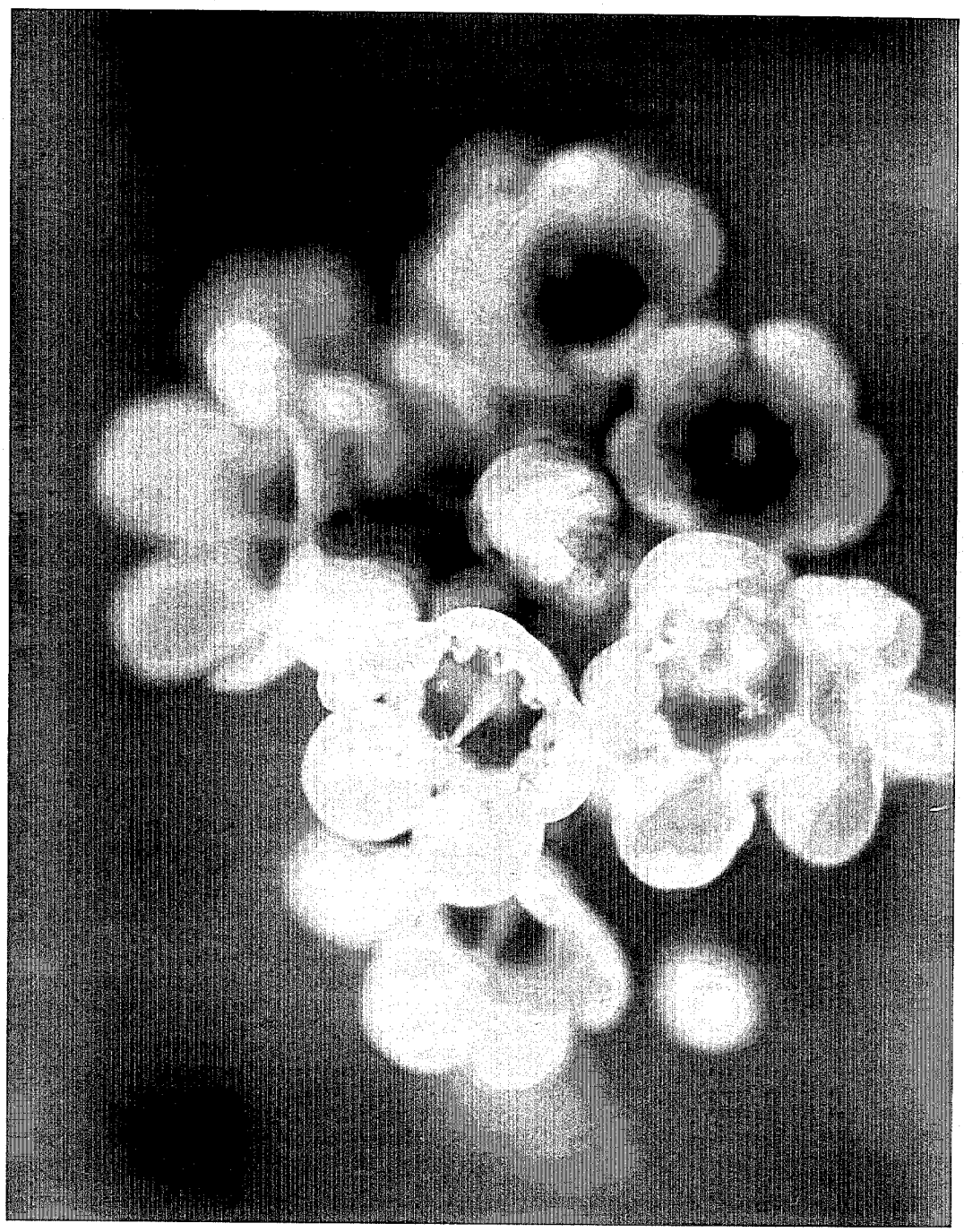

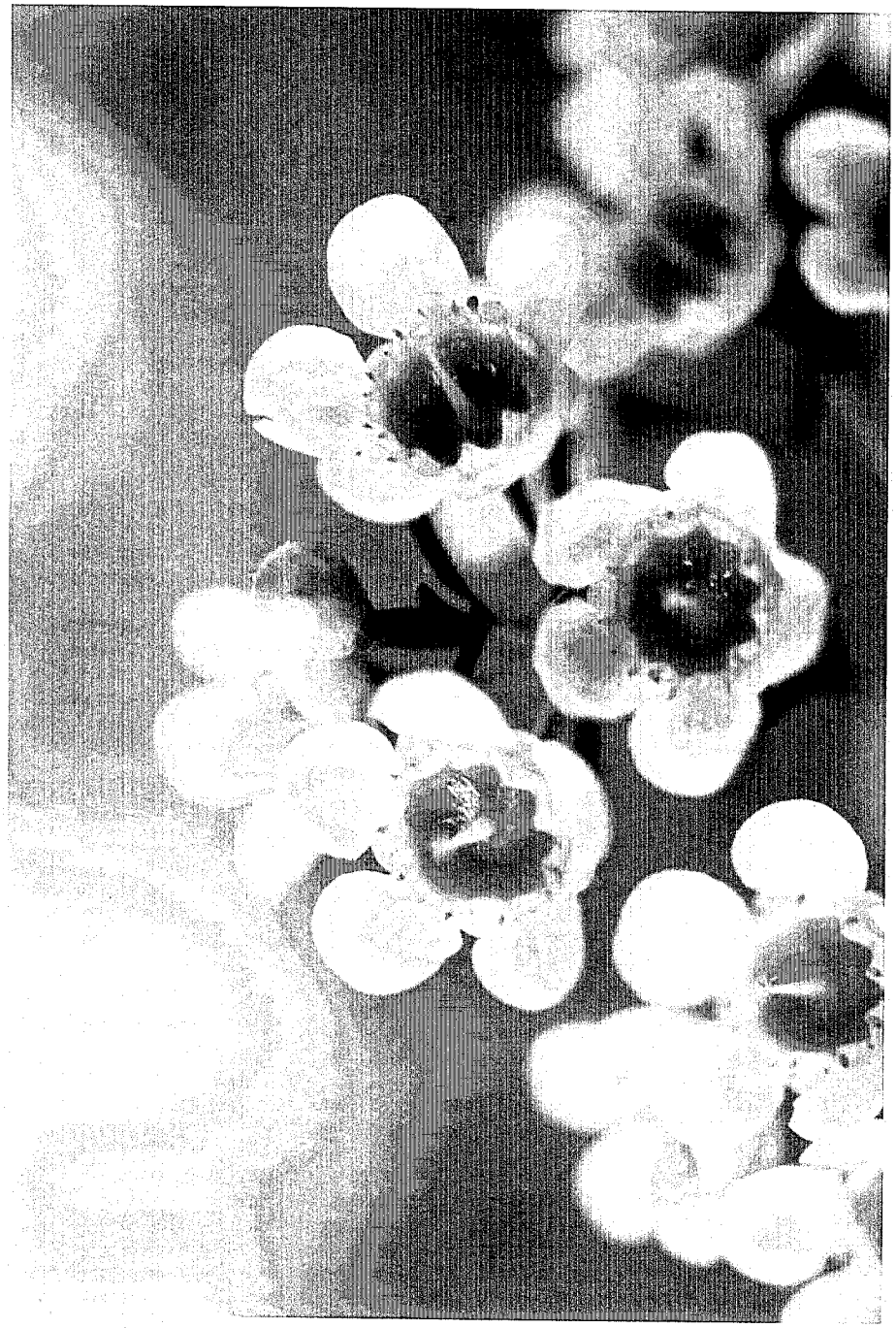

UNITED STATES PATENT AND TRADEMARK OFFICE

CERTIFICATE OF CORRECTION

PATENT NO. : Plant 8,791

DATED : June 21, 1994

INVENTOR(S) : Brian Jack; Victoria Syme

It is certified that error appears in the above-indentified patent and that said Letters Patent is hereby corrected as shown below:

On the title page:

After "[58]" insert the following reference:
-- [56] Reference Cited
U.S. PATENT DOCUMENT
P.P. 1,101 6/1952 Schilt...Plt. 54.1 --.

Column 2, line 34, change "marrow" to -- narrow --.

Signed and Sealed this

Eighteenth Day of October, 1994

*Attest:*

*Attesting Officer*

BRUCE LEHMAN

*Commissioner of Patents and Trademarks*